(12) United States Patent
Hietala et al.

(10) Patent No.: US 11,795,124 B2
(45) Date of Patent: Oct. 24, 2023

(54) RENEWABLE ALKENE PRODUCTION ENGAGING METATHESIS

(71) Applicant: Neste Oyj, Espoo (FI)

(72) Inventors: Jukka Hietala, Porvoo (FI); Anja Leminen, Porvoo (FI); Virpi Rämö, Porvoo (FI); Jukka Räsänen, Porvoo (FI)

(73) Assignee: Neste Oyj, Espoo (FI)

( * ) Notice: Subject to any disclaimer, the term of this patent is extended or adjusted under 35 U.S.C. 154(b) by 0 days.

(21) Appl. No.: 17/762,893

(22) PCT Filed: Sep. 25, 2020

(86) PCT No.: PCT/FI2020/050631
§ 371 (c)(1),
(2) Date: Mar. 23, 2022

(87) PCT Pub. No.: WO2021/058876
PCT Pub. Date: Apr. 1, 2021

(65) Prior Publication Data
US 2022/0363613 A1 Nov. 17, 2022

(30) Foreign Application Priority Data
Sep. 26, 2019 (FI) ...................................... 20195820

(51) Int. Cl.
C07C 6/04 (2006.01)
C07C 67/02 (2006.01)
(Continued)

(52) U.S. Cl.
CPC ............... *C07C 6/04* (2013.01); *C07C 67/02* (2013.01); *C07C 67/333* (2013.01); *C07C 67/54* (2013.01); *C10G 7/00* (2013.01); *C10M 101/04* (2013.01)

(58) Field of Classification Search
CPC .. C07C 6/04; C07C 11/02; C07C 7/13; C07C 1/213; C07C 9/14; C07C 9/22;
(Continued)

(56) References Cited

U.S. PATENT DOCUMENTS

| | | | |
|---|---|---|---|
| 3,823,070 A | 7/1974 | Minato et al. | |
| 3,912,586 A | 10/1975 | Kaneyuki et al. | |

(Continued)

FOREIGN PATENT DOCUMENTS

| | | |
|---|---|---|
| CN | 101360810 A | 2/2009 |
| CN | 101868552 A | 10/2010 |

(Continued)

OTHER PUBLICATIONS

Office Action dated May 11, 2022, by the Canadian Patent Office in corresponding Canadian Patent Application No. 3,149,520. (4 pages).
(Continued)

*Primary Examiner* — Sharon Pregler
(74) *Attorney, Agent, or Firm* — BUCHANAN, INGERSOLL & ROONEY PC

(57) ABSTRACT

Herein is provided a process for producing renewable products, such as alkenes, from a feedstock of biological origin. The process includes subjecting a feedstock including fatty acid glycerides and optionally free fatty acids, wherein at least one hydrocarbon chain is unsaturated, to esterification reaction in the presence of an alcohol. The ester stream thereby obtained is then fractionated and a fraction including esters of unsaturated C18 fatty acids is subjected to metathesis conditions in the presence of an alkene to obtain metathesis products. Fractionation of the metathesis products includes recovery of at least renewable 1-decene, and unsaturated C10-C15 fatty acid esters.

21 Claims, 2 Drawing Sheets

(51) Int. Cl.
 *C07C 67/333* (2006.01)
 *C07C 67/54* (2006.01)
 *C10G 7/00* (2006.01)
 *C10M 101/04* (2006.01)

(58) Field of Classification Search
 CPC ..... C07C 29/132; C07C 29/147; C07C 67/02; C07C 67/343; C07C 67/347; C07C 67/58; C07C 6/02; C10L 1/026; C10L 1/08; C10L 1/00; C10L 1/02; C10L 2200/0469; C10L 2200/0476
 See application file for complete search history.

(56) References Cited

U.S. PATENT DOCUMENTS

| | | | | |
|---|---|---|---|---|
| 7,256,301 | B2* | 8/2007 | Erguen | C11C 3/003 554/167 |
| 8,580,985 | B2 | 11/2013 | Thompson et al. | |
| 8,753,853 | B2 | 6/2014 | Ritter et al. | |
| 9,023,626 | B2 | 5/2015 | Dubois | |
| 9,676,884 | B2 | 6/2017 | Rizvi et al. | |
| 11,021,416 | B2 | 6/2021 | Bosetti et al. | |
| 11,459,280 | B2 | 10/2022 | Bosetti et al. | |
| 2004/0082042 | A1 | 4/2004 | Staley | |
| 2005/0284940 | A1 | 12/2005 | Enomoto et al. | |
| 2006/0079704 | A1 | 4/2006 | Lacombe et al. | |
| 2007/0131579 | A1 | 6/2007 | Koivusalmi et al. | |
| 2007/0135663 | A1 | 6/2007 | Aalto et al. | |
| 2010/0191008 | A1 | 7/2010 | Olson | |
| 2010/0305354 | A1 | 12/2010 | Dubois | |
| 2011/0113679 | A1 | 5/2011 | Cohen et al. | |
| 2011/0300594 | A1 | 12/2011 | Ritter et al. | |
| 2012/0197032 | A1 | 8/2012 | Firth et al. | |
| 2012/0253069 | A1 | 10/2012 | Zang et al. | |
| 2013/0217906 | A1 | 8/2013 | Kunz et al. | |
| 2013/0225409 | A1 | 8/2013 | Allen et al. | |
| 2013/0225473 | A1 | 8/2013 | Allen et al. | |
| 2014/0005423 | A1 | 1/2014 | Allen et al. | |
| 2014/0031592 | A1* | 1/2014 | Shinde | C07C 45/455 585/324 |
| 2014/0228586 | A1 | 8/2014 | Beardslee et al. | |
| 2014/0275595 | A1 | 9/2014 | Wampler et al. | |
| 2015/0087521 | A1 | 3/2015 | Allen et al. | |
| 2015/0210855 | A1 | 7/2015 | Firth et al. | |
| 2015/0353996 | A1 | 12/2015 | Hoo et al. | |
| 2015/0361024 | A1 | 12/2015 | Laplaza | |
| 2016/0251278 | A1 | 9/2016 | Bosetti et al. | |
| 2016/0298145 | A1 | 10/2016 | Laplaza et al. | |
| 2016/0340616 | A1 | 11/2016 | Littich et al. | |
| 2017/0137365 | A1 | 5/2017 | Wampler et al. | |
| 2019/0071611 | A1 | 3/2019 | Goossen et al. | |
| 2020/0181503 | A1 | 6/2020 | Myllyoja et al. | |
| 2020/0181504 | A1 | 6/2020 | Myllyoja et al. | |
| 2020/0181527 | A1* | 6/2020 | Kulmala | B01D 3/143 |
| 2021/0171420 | A1 | 6/2021 | Bosetti et al. | |
| 2022/0009855 | A1 | 1/2022 | Myllyoja et al. | |
| 2022/0340835 | A1 | 10/2022 | Myllyoja et al. | |
| 2022/0356131 | A1 | 11/2022 | Hietala et al. | |

FOREIGN PATENT DOCUMENTS

| | | | |
|---|---|---|---|
| CN | 102439118 A | 5/2012 | |
| CN | 102498086 A | 6/2012 | |
| CN | 102770520 A | 11/2012 | |
| CN | 102781583 A | 11/2012 | |
| CN | 104837802 A | 8/2015 | |
| CN | 105189576 A | 12/2015 | |
| CN | 106170530 A | 11/2016 | |
| CN | 107001217 A | 8/2017 | |
| EP | 1741768 A1 | 1/2007 | |
| EP | 2155838 B1 | 9/2014 | |
| ES | 2595106 T3 * | 12/2016 | C07C 51/43 |
| FI | 100248 B | 10/1997 | |
| WO | 0017380 A1 | 3/2000 | |
| WO | 0104337 A1 | 1/2001 | |
| WO | 0121572 A1 | 3/2001 | |
| WO | 2007068795 A1 | 6/2007 | |
| WO | 2007068796 A2 | 6/2007 | |
| WO | 2007068796 A3 | 8/2007 | |
| WO | 2008046106 A2 | 4/2008 | |
| WO | 2008048522 A1 | 4/2008 | |
| WO | 2008140468 A2 | 11/2008 | |
| WO | 2010068904 A2 | 6/2010 | |
| WO | 2011046872 A2 | 4/2011 | |
| WO | 2011056881 A2 | 5/2011 | |
| WO | 2012061093 A1 | 5/2012 | |
| WO | 2012129477 A1 | 9/2012 | |
| WO | 2014058867 A1 | 4/2014 | |
| WO | 2015108874 A1 | 7/2015 | |
| WO | 2016014417 A1 | 1/2016 | |
| WO | 2016062868 A1 | 4/2016 | |
| WO | 2018234187 A1 | 12/2018 | |

OTHER PUBLICATIONS

Ahmad, F. B. H., et al., "Co-Metathesis Reaction of Crude Palm Oil and Ethene", JAOCS, 1995, vol. 72, No. 6, pp. 757-758, AOCS Press. (2 pages).
Alm, M., "Animal Fats", 2013, AOCS Lipid Library [online]. Available at https://lipidlibrary.aocs.org/edible-oilprocessing/animal-fats [Accessed Aug. 27, 2019]. (21 pages).
Bosma, R. H. A., et al., "Cometathesis of Methyl Oleate and Ethylene; a Direct Route to Methyl Dec-9-enoate", J. C. S. Chem. Comm., 1981, pp. 1132-1133. (2 pages).
Chikkali, S. et al., "Refining of Plant Oils to Chemicals by Olefin Metathesis", Angew. Chem. Int. Ed., 2012, vol. 51, pp. 5802-5808, Wiley Online Library, Wiley-VCH Verlag GmbH & Co. KGaA, Weinheim, DE. (7 pages).
Communication of Acceptance under section 29a of Patents Decree issued in corresponding Finnish Patent Application No. 20195820 by the Finnish Patent and Registration Office dated Sep. 15, 2020. (3 pages).
Communication of Acceptance under section 29a of Patents Decree issued in corresponding Finnish Patent Application No. 20195822 by the Finnish Patent and Registration Office dated Sep. 15, 2020. (3 pages).
Communication of Acceptance under section 29a of Patents Decree issued in corresponding Finnish Patent Application No. 20195823 by the Finnish Patent and Registration Office dated Sep. 15, 2020. (3 pages).
Finnish Search Report for Finnish Patent Application No. 20195823 dated Jan. 23, 2020 (3 pages).
Finnish Search Report for Finnish Patent Application No. 20195820 dated Jan. 24, 2020 (4 pages).
Finnish Search Report for Finnish Patent Application No. 20195822 dated Jan. 24, 2020 (3 pages).
International Search Report (PCT/ISA/210) and Written Opinion (PCT/ISA/237) dated Nov. 20, 2020, by the European Patent Office as the International Searching Authority for International Application No. PCT/FI2020/050630. (16 pages).
International Search Report (PCT/ISA/210) and Written Opinion (PCT/ISA/237) dated Nov. 20, 2020, by the European Patent Office as the International Searching Authority for International Application No. PCT/FI2020/050631. (16 pages).
International Search Report (PCT/ISA/210) and Written Opinion (PCT/ISA/237) dated Dec. 16, 2020, by the European Patent Office as the International Searching Authority for International Application No. PCT/FI2020/050632. (17 pages).
Lee, H. et al., "Biotransformation of dicarboxylic acids from vegetable oil-derived sources: current methods and suggestions for improvement", Applied Microbiology and Biotechnology, 2019, vol. 103, pp. 1545-1555. (11 pages).
Mandelli, D. et al., "Ethenolysis of Esters of Vegetable Oils: Effect of B2O3 Addition to Re2O7/SiO2.Al2O3—SnBu4 and CH3ReO3/SiO2.Al2O3 Metathesis Catalysts", JAOCS, 1996, vol. 76, No. 2, pp. 229-232, AOCS Press. (4 pages).

(56) References Cited

OTHER PUBLICATIONS

Metzger, J. O., "Fats and oils as renewable feedstock for chemistry", Eur. J. Lipid Sci. Technol., 2009, vol. 111, pp. 865-876. (13 pages).

Millican, R. C., et al., "The Isolation and Properties of Some Naturally Occurring Octadecenoic (Oleic) Acids", J. Biol. Chem., 1944, vol. 154, pp. 437-450. (15 pages).

Mobley, D. P., "Biosynthesis of Long-Chain Dicarboxylic Acid Monomers From Renewable Resources—Final Technical Report", DE-FC36-95G010099, Apr. 1999 (178 pages).

Mol, J. C., et al., "Metathesis in Oleochemistry", J. Braz. Chem. Soc., 1998, vol. 9, No. 1, pp. 1-11, Soc. Bras. Química. (11 pages).

Spekreijse, J., et al., "The Future of Ethenolysis in Biobased Chemistry", ChemSusChem, 2017, vol. 10, pp. 471-482, Wiley Online Library, Wiley-VCH Verlag GmbH & Co. KGaA, Weinheim, DE. (13 pages).

Warwel, S., et al., "Polymers and surfactants on the basis of renewable resources", Chemosphere, 2001, vol. 43, pp. 39-48, Elsevier Science Ltd. (10 pages).

Watthanasringkarn, S., et al., "Synthesis of Lubricant from Methyl Ester Palm Stearin", Int'l Journal of Research in Chemical, Metallurgical and Civil Eng., 2015, vol. 2, No. 1, pp. 9-12. (4 pages).

Wheeler, D. H., et al., "The Preparation and Properties of Highly Purified Methyl Oleate", Oil and Soap, Nov. 1939, vol. 16, No. 11, pp. 207-209. (3 pages).

Woo-Young, Jeon, et al.., "Microbial production of sebacic acid from a renewable source: production, purification, and polymerization", Green Chemistry, vol. 21, No. 23, Jan. 2019, pp. 6491-6501. (11 pages).

Wyrębek, P. et al., "Looking for the Noncyclic(amino)(alkyl)carbene Ruthenium Catalyst for Ethenolysis of Ethyl Oleate: Selectivity is on Target", ACS Omega, Dec. 27, 2018, vol. 3, pp. 18481-18488, ACS Publications. (15 pages).

Churi et al., "A study of metathesis of unsaturated carboxylic esters", Journal of the Oil Technologists Association of India, vol. 25, No. 4, Jan. 1, 1993, pp. 93-95.

Notice of First Office Action dated Oct. 31, 2022, by the Chinese Patent Office in corresponding Chinese Patent Application No. 202080066719.9, with an English translation of the Notice. (17 pages).

Office Action (Notice of First Office Action) dated Oct. 19, 2022, by the Chinese Patent Office in corresponding Chinese Patent Application No. 202080066686.8, and an English Translation of the Office Action. (19 pages).

Office Action (Notice of First Office Action) dated Oct. 31, 2022, by the Chinese Patent Office in corresponding Chinese Patent Application No. 202080066719.9, and an English Translation of the Office Action. (17 pages).

Office Action dated Sep. 16, 2022, by the U.S. Patent and Trademark Office in U.S. Appl. No. 17/762,894. (6 pages).

Office Action dated Oct. 12, 2022, by the U.S. Patent and Trademark Office in U.S. Appl. No. 17/762,974. (13 pages).

Office Action dated Dec. 14, 2022, by the National Intellectual Property Office of China in corresponding Chinese Patent Application No. 202080066687.2, and a machine English translation of the Office Action. (16 pages).

* cited by examiner

RENEWABLE ALKENE PRODUCTION ENGAGING METATHESIS

FIELD OF THE INVENTION

The present disclosure relates to a process for producing renewable products, such as renewable alkenes, in particular to processes including a metathesis reaction of an unsaturated fatty acid ester with alkenes, preferably renewable alkenes. Further, herein is provided a method relating to more efficient biomass utilisation in production of alkenes with desired carbon number through utilisation of the C=C double bonds naturally occurring in the feedstock. More specifically, the present disclosure relates to production of selected renewable alkenes, for example 1-decene.

BACKGROUND OF THE INVENTION

Renewable feedstocks present a sustainable alternative to petrochemical sources. The renewable feedstocks have been derived from e.g. variety of vegetable oils, animal fats, recycled waste oils and even microbial oils. Hydrotreated vegetable oils such as palm oil, derivatives thereof, animal fat and other wastes or residues have been the major feedstock dominating the global renewable fuel market. The present process is related to combined production of renewable base oil and alkenes from the same or similar feedstocks of biological origin.

Hydrotreating is an efficient process, but when applied to feedstock originating from renewable materials, it does not utilize the natural characteristics of the feedstock in the most elegant way. For example, reduction of triglycerides into paraffinic hydrocarbons involves saturation of C=C double bonds and loss of all oxygen containing functionalities even though they could be useful and valuable in certain other product fractions. Therefore, there is a need for more sophisticated overall processes, wherein feedstock characteristics are better taken into consideration, and utilized even more efficiently to produce a wider spectrum of high value products. Further, there is a need for avoiding excessive hydrogen consumption. Yet, there still is a need to minimize possible oxygen-containing high value compounds ending up in lower value hydrocarbon products.

Metathesis was first reported in the literature two decades ago. Since then, is has been studied for various compounds and corresponding results published. It has been suggested to olefin metathesis to convert oleo-chemicals into value-added products such as the bifunctional molecule methyl 9-decenoate. However, low ethenolysis efficiency and a need for peroxide-scavenging feedstock pretreatment have decreased the overall interest.

One example of published metathesis reports is an international patent application publication WO2008046106 A2. It aims at development of a process for producing terminal olefins from internal olefins, especially from a variety of olefinic sources. In the experimental part it studies the reactions referred to as ethenolysis, propenolysis and butenolysis using soy FAME as model material. With regard to FAME referred therein, no attention is paid to saturated fatty acid esters flowing through the metathesis reactor as inerts. A need for impurity removal before metathesis reaction is acknowledged and different purification means studied, many of which clearly applicable to laboratory conditions only.

Another patent application, WO2008048522 A1, more specifically claim 1 therein, discloses subjecting polyunsaturated starting material to cross-metathesis and aims at the recovery of monounsaturated alkene composition. The experimental part of said document reveals that the yields of 9DA and 9UDA stay between 50 and 70% at its best, typically below 50%. The metathesis products recovered are subjected to separations to improve purity. It seems to be accepted that part of the feed is anyway lost.

Two patent applications, US20130217906 A1 and US20140275595 A1 by the same applicant provide details for an overall process of natural oils, such as vegetable oils, subjected to metathesis and subsequent recovery of methyl 9-decenoate. The metathesis products were further processed by separations, partial hydrogenation, and optionally, by further conversion of said methyl 9-decenoate to dimethyl octadec-9-en-dicarboxylate.

Metathesis has been studied also academically. Wyrebek, P. et al, ACS Omega Vol. 3, pp. 18481-88 (2018) published a laboratory study on 65 metathesis catalysts. At a 1 L scale, ethyl oleate as substrate and a metathesis catalyst were reacted under the ethylene pressure of 20 bar for 2 h. The conversion was 56%. The reaction mixture was treated with a metal scavenger and vacuum distilled. Interesting information on metathesis side products was obtained, but they concluded that the preliminary experiments at only 1 L scale cannot be used to assess the economic validity of the commercial-scale ethenolysis process. Hence, there is a need for a process for alkene production from a glyceride containing feedstock wherein feedstock pretreatment can be at least simplified, preferably avoided. Further, there is a need to improve metathesis efficiency. Further, there is a need to use the feedstock efficiently, such as by producing further products in addition to metathesis products.

SUMMARY OF THE INVENTION

To overcome at least some of the problems of the prior art, herein is provided a novel process for renewable alkene production from a glyceride containing feedstock, the process comprising:

a) providing the glyceride containing feedstock comprising free fatty acids, fatty acid glycerides selected from monoglycerides, diglycerides and triglycerides of fatty acids, or a mixture thereof, wherein the feedstock contains a compound having at least one carbon-carbon double bond;

b) subjecting the feedstock to esterification reaction, preferably selected from esterification of fatty acids and transesterification of mono- di- or triglycerides or a combination thereof, in the presence of a C1-C4 mono-alcohol, to yield a fatty acid ester stream;

c) subjecting the product from step b) to fractional distillation to provide at least three fractions, namely, a gas fraction comprising water and C1-C4 alcohols; a fraction comprising fatty acid esters up to C16 for producing renewable base oil meeting the API group III specifications; and a fraction comprising unsaturated C18 fatty acid esters;

d) subjecting the fraction comprising unsaturated C18 fatty acid esters to metathesis reaction conditions in the presence of a C2-C4 alkene to obtain metathesis products comprising renewable alkenes, such as 1-decene, and fatty acid derived esters, such as alkyl-9-decenoate;

e) recovery of at least one renewable alkene, comprising 1-decene and at least one fatty acid derived ester, comprising alkyl-9-decenoate, from products of step d.

The present inventors have found that a glyceride containing feedstock comprising free fatty acids, fatty acid glycerides selected from monoglycerides, diglycerides and triglycerides of fatty acids, or a mixture thereof, can be refined to renewable alkenes by subjecting only a fraction comprising unsaturated C18 fatty acid esters of said feedstock to metathesis reaction. In addition to advantages related to improved efficiency within the metathesis reaction, a further advantage is achieved when the fractional distillation as thermal separation contributes to removal of metathesis catalyst poisons.

As explained in detail below, further advantages are obtainable through other embodiments of the processes and uses.

BRIEF DESCRIPTION OF THE DRAWINGS

The invention will be described in more detail by means of preferred embodiments. Reference is made to the following FIGS. 1 and 2.

DETAILED DESCRIPTION OF THE INVENTION

The present disclosure provides a process for producing renewable alkenes from a glyceride containing feedstock.

The present disclosure is described with the aid of the following three embodiments. The general process according to claim 1 is described with reference to FIG. 1. A preferred embodiment depicting the details of the process is described with reference to FIG. 2.

The steps and specific features of this overall process are next discussed in detail.

Figure 1:
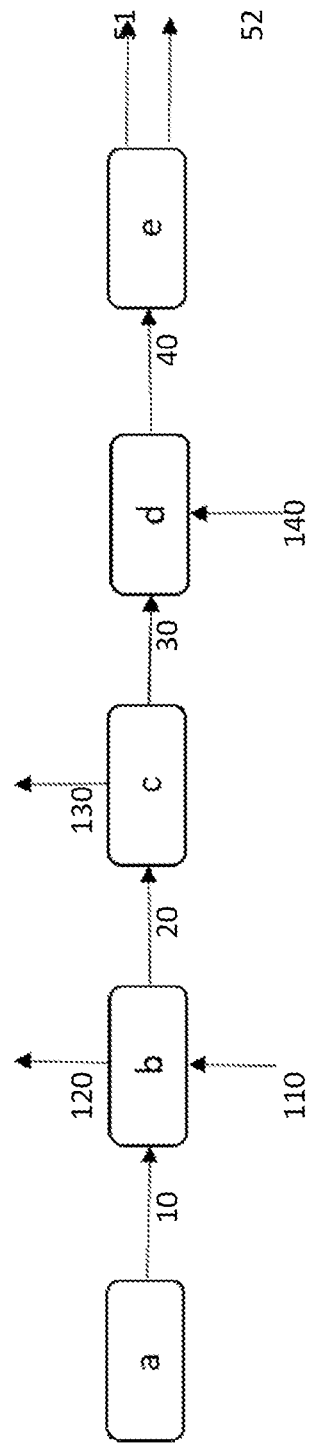
FIG. 1 depicts the overall process of the present disclosure.

According the FIG. 1, a suitable and/or desired feed (a) containing unsaturated fatty acids and/or glycerides (10) is directed to esterification (b) in order to convert the possible fatty acids therein into esters, and/or to transesterification (b) for transforming the possible esters contained in the feed, such as mono- di- or triglycerides or a combination thereof, into more suitable/desired esters in the presence of an alcohol (110) which is entered into the esterification thereby forming glycerol (120). The formed fatty acid esters (20) are subjected to thermal separation (c), by fractional distillation, whereby the unsaturated C18 or longer chained fatty acid esters (30) are separated from the C1-C16 compounds (130). The fraction comprising the unsaturated C18 fatty acid esters (30) is directed to metathesis (d) reaction conditions in the presence of a C2-C4 alkene (140) to obtain metathesis products (40) comprising renewable alkenes, such as 1-decene (51), and fatty acid derived esters, such as alkyl-9-decenoate (52). The metathesis products are separated from each other, preferably by distillation (e), into final products, which may be used for several different applications. Other fractions obtainable from distillation (e) are not shown here.

Figure 2:
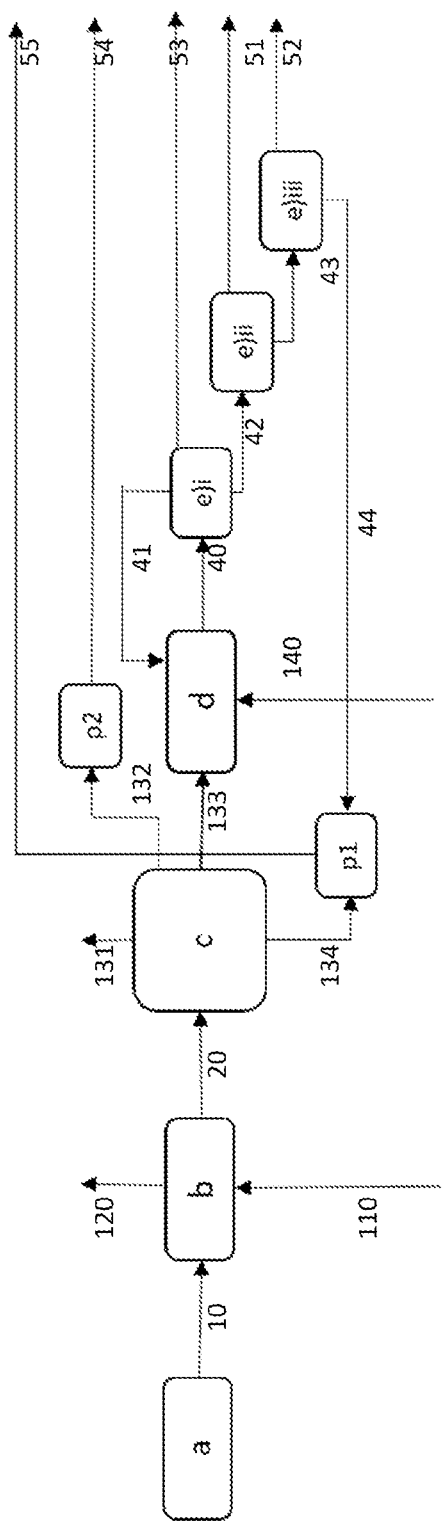
FIG. 2 depicts a detailed preferred embodiment of the present disclosure.

In an embodiment according to FIG. 2, a suitable and/or desired feed (a) containing unsaturated fatty acids and/or glycerides (10) is directed to esterification (b) in order to convert the possible fatty acids therein into esters, and/or to transesterification (b) for transforming the possible esters contained in the feed, such as mono- di- or triglycerides or a combination thereof, into more suitable/desired esters in the presence of an alcohol (110) which is entered into the esterification thereby forming glycerols (130). The formed fatty acid esters (20) are subjected to thermal separation (c) by fractional distillation. A multistage distillation is used to separate the fatty acid esters into fractions comprising the light C1-C10 (131) compounds, C12-C16 fatty acid esters (132), C18 unsaturated fatty acid esters (133) and the bottom product (134) which includes the heavier >C18 fatty acid esters. The fraction comprising the unsaturated C18 fatty acid esters (133) is directed to metathesis (d) reaction conditions in the presence of a C2-C4 alkene (140) to obtain the metathesis products (40). The metathesis products are further separated from each other into at least three different fractions: The first product is recovered by evaporation (e)i) comprising alkenes (53). The light alkenes (41) therefrom may be recycled back to the metathesis (d) reaction conditions whereas C5-C9 alkenes (53) are used as renewable chemicals or fuel components. The second product is obtained by directing the evaporation bottom (42) to a first product distillation (e)ii). The distillate yields 1-decene (51). The third product is alkyl-9-decenoate (52) recovered as distillate from a second product distillation (e)iii). The C12-C16 fatty acid esters (132) recovered in the thermal separation (c) are directed to ketonisation and hydrotreatment (p2) for the manufacture of renewable base oil (54). And the bottom product (134) including the heavier >C18 fatty acid esters is directed to hydrotreatment (p1) together with the second distillation bottom (44) for the manufacture of renewable fuels (55).

A specific embodiment described in detail provides an example including specific feedstock with selected chemicals. This embodiment provides a process using palm oil as feedstock with selected reagents with references corresponding to FIG. 2.

In an exemplary embodiment, palm oil is used as the feed containing saturated palmitic acid C16, stearic acid C18 and some lauric C12 and myristic C14 acids, and unsaturated oleic acid C18:1 and linoleic acid C18:2 which form triglycerides with glycerol. The crude palm oil is first purified to remove all possibly harmful impurities. The purified palm oil feed (a) is subjected to transesterification (b) for transforming the triglycerides into ethyl esters in the presence of ethanol. Ethanol is entered (110) into the esterification thereby releasing glycerol (130). The formed palmitic acid C16, stearic acid C18, lauric acid C12, myristic acid C14, oleic acid C18:1 and linoleic acid C18:2 ethyl esters (20) are subjected to thermal separation (c) by fractional distillation. The obtained fractions include a light C1-C10 (131) fraction, C12-C16 saturated ethyl esters (132), C18:0, C18:1 and C18:2 ethyl esters (133) and the bottom product (134) which includes the heavier >C18 fatty acid ethyl esters. The C18 fatty acid ethyl esters (133) are directed to metathesis (d) reaction conditions in the presence of ethene (140) to obtain the metathesis products (40), wherein 1-decene and 9-DAEE are prevailing. The formed products are separated into the following fractions: alkenes (53) recovered by evaporation (e)i) wherefrom the excess ethene (41) is recycled back to metathesis (d); The evaporation bottom (42) is directed to a first product distillation (e)ii) resulting in 1-decene (51); The third product, ethyl-9-decenoate (52) is recovered as distillate from the second product distillation (e)iii), whereas the second distillation bottom (44) is directed as feed into a hydrotreatment process (p1) together with the bottom product (134) including the heavier >C18 fatty acid esters. Hydrotreatment converts these streams into renewable fuels (55). The C12-C16 saturated fatty acid esters (132) recovered in the fractional distillation (c) are directed to ketonisation and subsequent hydrotreatment (p2) for the manufacture of renewable base oil (54).

The Glyceride Containing Feedstock

The feed to the present process is here defined as glyceride containing feedstock. The glyceride containing feedstock comprises free fatty acids, fatty acid glycerides selected from monoglycerides, diglycerides and triglycerides of fatty acids, or a mixture thereof. It is essential for the metathesis process that the feedstock contains a compound, in practice compounds, having at least one carbon-carbon double bond. Glyceride containing feedstocks are of biological origin. Biological fats and oils originating from plants, animals or fishes are naturally in form of glycerides, hence fatty acids are present as glycerol esters.

The glyceride containing feedstock suitable for use according to the present invention comprises free fatty acids and glycerides. Particularly suitable glyceride containing feedstocks for renewable base oil production, are those which comprise glycerides abundant with palmitic acid moieties, i.e. C16 fatty acid esters. In addition, the feedstock contains compounds having at least one carbon-carbon double bond, such as unsaturated fatty acid moieties. Typically, the feedstock further comprises C18:1 fatty acid moieties.

Several oils and fats contain significant amounts of C16 fatty acids. Partly the fatty acids are already in the form of free fatty acids (FFA), but partly they are bound to glycerin as esters.

Table 1 lists availability of some C16 and C18 free fatty acids from natural material sources, and the fatty acid carbon chain lengths and unsaturation of exemplary fats and oils found in the literature, possibly suitable for use in the process of the present invention.

wherein $R_1$, $R_2$ and $R_3$ ($R_x$) are the same or different and represent saturated or unsaturated C3-C27 hydrocarbon chains. The length of the hydrocarbon chain for $R_x$ is typically 17 carbons, and hence, they are referred to as C18 fatty acids. Another typical length of the hydrocarbon chain for IR, is 15 carbons with reference to C16 fatty acids. In general, typical carbon numbers of the fatty acids linked to the two other hydroxyl groups are even, being generally between carbon chain lengths from C12 to C22.

In addition to the prevailing triglycerides, some diglycerides and monoglycerides may be present as well. Diglycerides are esters of glycerol with two fatty acid molecules having alkyl groups $R_x$ and monoglycerides are ester of glycerol with one fatty acid molecules having an alkyl group $R_x$ bound therein. These mono- and diglycerides release glycerol in hydrolysis as well. Mono- and diglycerides are formed in minor amounts spontaneously from triglycerides during storage or under purification conditions, releasing some free fatty acids. Hence, the term as used herein "glyceride containing feedstock" refers to feed comprising mono-, di-, triglycerides and/or free fatty acids.

Prior to processing, the glyceride containing feedstock of biological origin should be pretreated with suitable known methods, such as thermally, mechanically for instance by means of shear force, chemically for instance with acids or

TABLE 1

Exemplary glyceride containing feedstocks suitable for the process for producing renewable chemicals and optionally renewable base oil, of the present invention.

| Fat/oil | 8:0 | 10:0 | 12:0 | 14:0 | 16:0 | 18:0 | 18:1 | 18:2 | 18:3 | 20:0 | 20:1 | 22:0 | 22:1 | Amount of FFAs [2]Amount of C16 and C18 FFAs |
|---|---|---|---|---|---|---|---|---|---|---|---|---|---|---|
| Canola | | | | 0.1 | 4.1 | 1.8 | 60.9 | 21.0 | | 0.7 | | 0.3 | | |
| Crude tall oil | | | | | [1]1-2 | | | | | | | | | |
| Cottonseed | | | 0.7 | | 21.6 | 2.6 | 18.6 | 54.4 | 0.7 | 0.3 | | 0.2 | | |
| Crumbe | | | | | 1.7 | 0.8 | 16.1 | 8.2 | 2.9 | 3.3 | | 2.2 | 59.5 | |
| Cuphea (PSR-23) | 0.8 | 81.9 | 3.2 | 4.3 | 3.7 | 0.3 | 3.6 | 2.0 | 0.3 | | | | | |
| Jatropha | | | | | [1]15 | | | | | | | | | 1.5-5 |
| Palm | | | 0.2 | 1.1 | 44.0 | 4.5 | 39.1 | 10.1 | 0.4 | 0.4 | | | | 4-7 |
| Palm Kernel | 3.3 | 3.4 | 48.2 | 16.2 | 8.4 | 2.5 | 15.3 | 2.3 | | 0.1 | 0.1 | | | |
| Palm stearin | | | | | [1]60 | | | | | | | | | 0.1 |
| PFAD | | | | | [1]45 | | | | | | | | | 75-88 |
| Rapeseed | | | | | 2.7 | 1.1 | 14.9 | 10.1 | 5.1 | 10.9 | | 0.7 | 49.8 | |
| Soybean | | | 0.1 | 0.2 | 10.7 | 3.9 | 22.8 | 50.8 | 6.8 | 0.2 | | | | 2.5 |
| Sunflower | | | | | 3.7 | 5.4 | 81.3 | 9.0 | | 0.4 | | | | 0.5 |
| Lard | | 0.1 | 0.1 | 1.5 | 26.0 | 13.5 | 43.9 | 9.5 | 0.4 | 0.2 | 0.7 | | | 5-10 |
| Tallow | | | 0.1 | 3.2 | 23.4 | 18.6 | 42.6 | 2.6 | 0.7 | 0.2 | 0.3 | | | 5-10 |

[1]Values measure at the Analytics lab of Neste Oyj by CG.
[2]Estimation of C16-C18 FFAs in %-wt is based on ½ * TAN (total acid number analysis), which is a fair approximation.

Typical basic structural unit of plant and fish oils and animal fats is a triglyceride. Triglyceride is an ester of glycerol with three fatty acid molecules having the structure below:

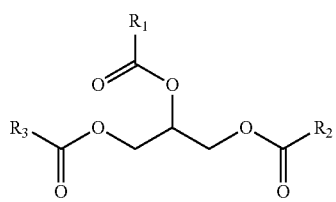

bases, or physically with radiation, distillation, cooling, or filtering. The purpose of chemical and physical pretreatments is to remove impurities interfering with the process or poisoning the catalysts, and to reduce unwanted side reactions. Hence, according to one embodiment, the glyceride containing feedstock is subjected to purification before entering into the esterification step. This purification may include e.g. degumming, bleaching and/or deodorizing.

Thus, glyceride containing feedstocks suitable for the process of the present invention comprise mono- di- and/or triglycerides and free fatty acids. Exemplary glyceride containing feedstocks are plant fats, plant oils, plant waxes, animal fats, such as lard, tallow, yellow grease, brown grease, animal oils, animal waxes, fish fats, fish oils, and fish waxes. Preferably, the glyceride containing feedstock originates from waste and/or residues of the mentioned exemplary glyceride containing feedstocks. More preferably, the waste and/or residues originate from sustainably-produced products, the production routes of which are traceable. Preferable feedstocks of animal origin are discussed in detail by Alm, M, (2013) Animal fats. [online]. Available at https://lipidlibrary.aocs.org/edible-oil-processing/animal-fats [Accessed 27.8.2019].

According to a specific embodiment, the "glyceride containing feedstock" comprises PFAD or consists of PFAD. PFAD (palm oil fatty acid distillate) is a processing residue from the refining of food-grade palm oil for the food industry uses. PFAD is considered as a waste or residue raw material.

When oil palm fruits are handled, normal bruising occurs causing the fat in the fruit to start degrading. The longer it takes for the fruit to be transported, processed, and refined into palm oil, the larger part of the fats degrade. When palm oil is being refined into food grade oil, these degraded fats, free fatty acids, are removed from the oil by distilling to improve taste, odor, and color of the oil, as well as to increase the shelf life. PFAD consists of these degraded components that are undesired for food production and need to be removed during the palm oil refining process before the oil meets the food industry's quality standards. PFAD as a by-product of physical refining of crude palm oil products is typically composed of free fatty acids (e.g. 81.7%), glycerides (e.g. 14.4%), squalene (0.8%), vitamin E (0.5%), sterols (0.4%) and other substances (2.2%). The composition may vary depending on i.e. geographical location of the raw material, growth conditions and the refining process, When the appropriate glyceride containing feedstock, optionally after pretreatment, is provided in step a, the next step, step b of the present process esterifies or transesterifies it to fatty acid esters.

Esterification

The feedstock as defined above, is subjected to esterification reaction. Esterification may comprise esterification of fatty acids in the presence of a C1-C4 monoalcohol to yield a fatty acid ester containing stream. When glycerides are present in the feedstock, this step comprises a transesterification of mono- di- or triglycerides or a combination thereof, in the presence of a C1-C4 monoalcohol to yield a fatty acid ester containing stream.

As used herein, references to carbon numbers of fatty acid esters disregard the carbon number of the residue originating from the alcohol. For example, ethyl palmitate ($C_{18}H_{36}O_2$) is referred to as C16 fatty acid ester, or C16 fatty acid ethyl ester, hence an ester wherein the fatty acid residue carbon chain length is C16 and the two other carbons originate from ethanol.

The glyceride containing feedstock is esterified before subjecting it to metathesis step. This is due to sensitivity of the metathesis reaction, wherein free fatty acids are not an optimal feed. Free fatty acids present in the feed need to be esterified prior to metathesis. In prior art processes wherein for example triglycerides are fed to metathesis, esterification would in theory not be needed. Triglycerides as feed to metathesis are not ideal either, because their higher viscosity slows down the reaction rate and their complex structure produces a high variety of products leading to complicated separations. However, glyceridic feeds tend to degrade spontaneously and produce fatty acids and peroxides harmful to metathesis catalysts. Therefore, processes wherein fatty acids are present as glycerides, need a pretreatment anyway.

Transesterification is a process well known in the art, i.e. for production of biodiesel, such as FAME (fatty acid methyl ester). Glycerides are reacted in the presence of an alcohol to fatty acid esters. A common alcohol is methanol, producing fatty acid methyl esters (FAME). If ethanol is used in transesterification, fatty acid ethyl esters (FAEE) are obtained. Catalysts suitable for such reactions are known in the art. Hence, the ester bonds between glycerol and fatty acids are cleaved releasing glycerol, but the fatty acid residues are still in form of esters. The separation of glycerol from fatty acid esters formed is known in the art. An effective way of removing excess alcohols and glycerol is extraction with water. During transesterification and downstream processing thereof, some water is accumulated to the glycerol stream. Aqueous glycerol may be further reacted to useful compounds, such as propane diols or propanols.

The monoalcohol used for esterification of step b is selected from C1-C4 alcohols hence, methanol, ethanol, 1-propanol, 2-propanol, 1-butanol and 2-butanol, or a mixture thereof, preferably from bio-based monoalcohols. Monoalcohol refers to alcohol comprising only one hydroxyl group. Bio-based ethanol is abundantly available from fermentation of sugars and carbohydrates. Bio-based propanols may be obtained from e.g. glycerol. In embodiments, where ketonisation is applied, the C2-C4 alcohols are preferred for esterification or transesterification providing synergistic advantages to the overall process since they produce alkenes in ketonisation reactions.

In one embodiment ethanol in esterification and ethene in metathesis correspondingly are used. Preferably, the ethanol is bioethanol. Such use is advantageous to the overall process and contributes to character of metathesis products as 100% renewable.

Esterification provides an advantage in transforming the glyceridic structures, possibly comprising up to three ester bonds, hence triesters and molecular weight typically about 700-900 g/mol, into smaller and simpler monoesters, the reactions and products of which have narrower variation in the following process steps. Therefore, the esterified stream is herein also referred as "more suitable/desired esters" when discussing the figures.

As a specific embodiment, the glyceride containing feedstock may be subjected to splitting, preferably hydrolysis before said esterification reaction. In said hydrolysis, glycerol and free fatty acids or fatty acid salts are released from mono-, di- and triglycerides. Possible fatty acid salts are converted to free acids before or during the esterification. Free fatty acids are the esterified. Combination of hydrolysis and esterification is an alternative to transesterification. Esterification of free fatty acids is preferably catalytic, carried out over homogenous or heterogenous catalysts, such as a zinc laurate or a zinc stearate catalyst.

Thermal Separation

The product obtained from esterification is subjected to thermal separation by fractional distillation to provide at least three fractions, namely, a gas fraction comprising water and C1-C4 alcohols; a fraction comprising fatty acid esters up to C16; and a fraction comprising unsaturated C18 fatty acid esters As used herein, the thermal separation refers to any separation methods using heating and separating compounds of the esterification product based on different boiling points. Such separation methods comprise various evaporation and distillation processes. In the present process, the first compounds to gasify and to separate from the liquids are water and alcohols used for esterification or transesterification.

The esters obtained from esterification are subjected to fractional distillation. Said distillation provides several fractions, which are directed to different processing steps. In addition to fractionation, the fractional distillation contributes to purity of each fraction recovered thereby improving catalyst performance and endurance in catalytic processes downstream from fractional distillation. This was found to be especially advantageous in the present case where said catalytic processes downstream comprise metathesis, where the purification prior to catalytic metathesis can be simplified. For the metathesis reaction, the fractional distillation recovers a fraction comprising unsaturated fatty acid esters comprising fatty acid esters having a carbon chain length of C18, in a cumulative amount of at least 80%-wt, preferably at least 90%-wt, of the total fraction weight.

Starting from the lightest components, a light fraction recovers mainly the monoalcohol used from esterification in step b. It further comprises water and eventual other light alcohols, such as C1-C4 monoalcohols. The fraction mainly consists of said alcohols and water, so that the cumulative amount thereof is at least 80%-wt of the total fraction weight, typically ≥90%-wt, or even ≥99%-wt of the total fraction weight. Alcohols recovered thereof may be recycled back to the esterification process.

The most interesting fraction recovered is the fraction comprising unsaturated C18 fatty acid esters, in an amount of at least 80%-wt of the total fraction weight. Unsaturated C18 fatty acid esters have at least one C=C double bond, and can be characterized as C18:1, C18:2 or C18:3 fatty acid esters. Typically the saturated C18 fatty acid esters, alkyl octadecanoates, are recovered in this fraction as well, but they nevertheless constitute a minor part, for example ≤10%-wt of this fraction. As the content of saturated compounds in the input to the metathesis reaction is relatively low, said reaction is not unnecessarily diluted. This is particularly advantageous considering the catalyst usage in metathesis. Higher concentration of double bonds increases the reaction rate and the catalyst is employed to maximal activity before losing its' activity.

The fractional distillation further yields a bottom product comprising higher boiling esters. With "higher boiling esters" is herein referred to esters having a boiling point above of that of C18 fatty acid esters, hence higher boiling esters typically having boiling points 400° C.

A further fraction comprises alkyl esters having a fatty acid carbon chain length of C16 or less. The fraction may be characterized as a light fraction, since it comprises the lightest esters. Typically, the predominant carbon chain lengths are from C12 to C16, of which C16 is the most abundant. This fraction may be characterized by comprising at least 80%-wt, preferably at least 90%-wt, more preferably at least 98%-wt fatty acid esters having a carbon chain length of C12-C16. According to a specific embodiment, this fraction is subjected to ketonisation.

The thermal separation of step c is conducted by fractional distillation at elevated temperature. The temperatures alone are sufficient to degrade peroxides harmful to metathesis catalysts as discussed in relation to prior art processes. Distillation provides a well-known, and reliable method for fractionation. The fractional distillation may comprise one or more distillations. Most preferably said distillation comprises at least one vacuum distillation. The distillation conditions of the thermal separation step c. are guided by the characteristics of the ester feed. The distillation conditions of step c comprise a pressure from 0.2 to 5 kPa, preferably from 0.2 to 1 kPa.

The fractional distillation may be realized by using at least one vacuum distillation column, preferably from two to four columns, which may be in series, depending on the accuracy needed for the separation and on the carbon number size distribution of the fatty acid ester feed to distillation, the feed type and quality.

The fractional distillation can be done in a single distillation step or in two or three or more distillation steps. The distillation further purifies the distillate streams from metals and other heavy impurities which will reside after distillation at the bottom fraction. The fractions comprising fatty acid esters remain pure due to the impurities remaining in the bottom product. When the excess water is subsequently separated from the glycerol, many impurities will be removed along with the aqueous phase. The bottom product is recovered and hydrotreated, optionally together with other similar streams, yielding paraffinic hydrocarbons. Due to fractional distillation, the bottom product does not contain glycerol, which reduces hydrogen consumption in comparison to prior art processes based on hydrotreatment of triglycerides.

According to a preferred embodiment, the fractional distillation to provides
- at least one fraction comprising water and C1-C4 monoalcohol, in a cumulative amount of at least 80%-wt of the total fraction weight;
- at least one fraction comprising saturated C12-C16 fatty acid esters in a cumulative amount of at least 80%-wt, preferably at least 90%-wt of the total fraction weight;
- at least one fraction comprising unsaturated C18 fatty acid esters
- an optional fractional distillation bottom product comprising >C18 fatty acid esters and glycerol.

Preferably, in the fraction comprising unsaturated C18 fatty acid esters, the amount of unsaturated C18 fatty acid esters is at least 80%-wt of the total fraction weight. As one aspect, the present invention provides a use of fractional distillation as pretreatment for metathesis reaction of fatty acid esters. Said use may further comprise renewable fuel production.

Optional Pretreatment Methods Prior to Metathesis

The present invention is based on surprising finding that thermal separation decomposes peroxides prior to metathesis and contributes to the removal of water-soluble impurities with aqueous phase. Hence, pretreatment as described in the prior are is not needed in the process according to the present invention.

Depending on the feedstock quality, the feedstock to the metathesis reaction may be additionally pretreated if specifically required. These pretreatments include possible further removal of alcohols and peroxides.

Alcohols are optionally removed before feeding fatty acid esters to the metathesis reaction. Preferably the overall process according to the present invention comprises at least one purification step between steps b and c. Such purification step comprises treatment with an adsorbent, with a metal alkyl compound, with a metal alkoxide compound, with a reducing agent or with an organic drying agent, a thermal treatment or a combination thereof.

Some metathesis catalysts are known to be sensitive to impurities. With high catalyst loadings, catalyst poisoning is not immediately observed. However, at the lower limit of catalyst loading, the relative concentration of trace impurities to catalyst becomes larger and activity suffers. One typical class of impurities are organic hydroperoxides, which can be formed in natural oils by oxidative ageing.

According to specific examples, a further pretreatment may comprise treatment with an adsorbent, with a metal alkyl compound, with a metal alkoxide compound, with a reducing agent or with an organic drying agent, or a combination thereof.

The fatty acid alkyl esters may be treated with the magnesium silicate, such as commercially available Magnesol. Is has been reported to improve metathesis efficiencies at low catalyst loadings. Another pretreatment option is triethylaluminium treatment alone or together with further compounds, such as $Ac_2O$. Yet another chemical pretreatment method comprises treatment with metal alkoxides, such as $Al(OiPr)_3$ and $Zr(OEt)_4$. As physical treatment for peroxide removal heating the feedstock to a temperature greater than 100° C. in the absence of oxygen may be used.

A combination of chemical and physical pretreatments may comprise for example thermal treatment together with an absorbent treatment.

Metathesis

The fraction comprising unsaturated C18 fatty acid esters obtained from fractional distillation, is next subjected to metathesis reaction conditions in the presence of a C2-C4 alkene to obtain metathesis products comprising renewable alkenes, at least 1-decene and fatty acid derived esters, comprising alkyl-9-decenoate.

Metathesis reaction is based on rearrangements around C=C double bonds of two molecules of starting materials. The present application of metathesis aims at producing shorter alkenes and esters from unsaturated fatty acid esters. This is achieved by reacting the fraction comprising unsaturated C18 fatty acid esters with a short chain alkene, such as a C2-C4 alkene to obtain metathesis products comprising renewable alkenes, such as 1-decene, and fatty acid derived esters. Depending on the alkene used, the length of the unsaturated fatty acids and the double bond position therein, a metathesis reaction between these components produces a mixture comprising C5-C12 alkenes and C6-C18 unsaturated esters. Saturated compounds, such as alkyl stearates (C18:0 esters), act as inerts and pass through metathesis reaction unreacted.

As recommended by IUPAC, alkene is used here to denote an unsaturated hydrocarbon that contains at least one carbon-carbon double bond. Carbon-carbon double bond, or C=C-bond is also referred to as olefinic bond. In some contexts, such as in reference to poly alpha olefins, olefin is herein used as synonym to alkene.

Metathesis is preferably conducted at a temperature from 20 to 120° C., a pressure from 0.1 to 3 MPa using at least one metathesis catalyst. These metathesis reaction conditions apply to step d.

The metathesis reaction can be catalyzed by one or more metathesis catalysts. Typically, fatty ester metathesis catalysts are homogeneous. In case they can catalyze side reactions in successive reaction steps, it is advantageous to remove them from the solution after metathesis. A non-limiting description of suitable metathesis catalysts include complexes of the type I and II:

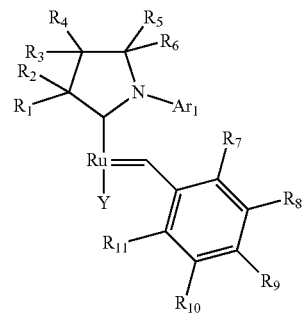

Wherein
$R_1$-$R_6$=same or different and selected from H, alkyl, cycloalkyl, alkenyl, aryl;
$Ar_1$=phenyl or benzene ring substituted with alkyl, cycloalkyl, alkenyl, Cl, Br, $OR_{12}$ ($R_{12}$=H, alkyl) or an aryl;
$R_7$-$R_{11}$=same or different and selected from H, alkyl, cycloalkyl, alkenyl, aryl, Cl, Br, $NO_2$, $OR_{13}$ ($R_{13}$=H, alkyl), $CH_2NR_{14}R_{15}$ ($R_{14}$, $R_{15}$=alkyl, benzyl, aryl); Y=N $R_{16}R_{17}$ ($R_{16}$, $R_{17}$=alkyl, benzyl, $CH_2$-aryl), $OR_{18}$ ($R_{18}$=alkyl).

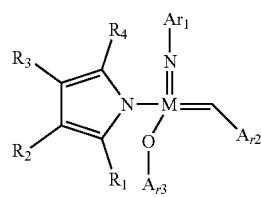

In complex II:
wherein M=Mo or W;
$R_1$-$R_4$=same or different and selected from H, alkyl, cycloalkyl, alkenyl, aryl, Cl, Br, OR' (R'=H, alkyl);
$Ar_1$, $Ar_2$, $Ar_3$=same or different and selected from phenyl or benzene substituted with alkyl, cycloalkyl, alkenyl, Cl, Br, OR" (R"=H, alkyl) or an aryl.

In prior art, alkylidene complex metathesis catalysts comprising a group 8 transition metal are reported. Said metal is preferably selected from ruthenium, molybdenum, osmium, chromium, rhenium, tungsten. Alkene in high purity, typically >99% by weight is fed to metathesis reactor, preferably in excess, to avoid self-metathesis of the feed components. Such catalysts are needed in low quantities, for example less than 150 ppm, less than 10 ppm or less than 5 ppm, for Ru catalysts, even from 2 to 4 ppm, as calculated by weight against the fatty acid ester fraction weight fed to metathesis. Catalyst quantity is optimized based on mass transfer to provide to the catalyst continuously more unreacted Metathesis is a reaction between two compounds having at least one C=C double bond each. In the present process, metathesis is used for cutting fatty acid structures having carbon numbers typically C18, to molecules having lower carbon numbers with the aid of C2-C4 alkenes, hence the shortening of said fatty acid structure. Hence, the C2-C4 alkenes are considered as metathesis reagents and used in excess. The metathesis reagent may be selected from ethene, propene and butenes (1-butene and 2-butene).

Ethene and 2-butene provide advantages through their symmetry, which results in lower product variation. To enable good control of the reactions, typically only one type of alkene at a time is applied. The preferred C2-C4 alkene is ethene. Metathesis with ethene produces alpha olefins and unsaturated fatty acids with the carbon-carbon double bond at terminal position, as metathesis products. Hence, they are particularly useful e.g. as polymerisation precursors.

It is considered especially advantageous to use renewable C2-C4 alkene as reagent for metathesis reaction. According to a specific embodiment, this is possible through a combination of a metathesis reaction with a ketonisation reaction releasing renewable alkenes in the same overall process. Accordingly, according to a preferred embodiment, alkenes recovered from a ketonisation reaction of C16 fatty acid ethyl esters are recycled and used in the metathesis reaction.

This can be exemplified with ethene. According to an embodiment, ethene is used as the metathesis reagent, originating from renewable ethanol esterified to fatty acids in esterification or transesterification reaction. In the ketonisation reaction between two fatty acid ethyl esters, such as two C16 fatty acid ethyl esters, renewable ethene originating from said ethanol, is formed. This ethene may be recycled back to the metathesis reaction.

Further, ethene recovered through flash or evaporation after metathesis reaction is preferably recycled back to metathesis reaction.

In embodiments using ethene as reagent, the main reaction taking place is formation of 1-decene and ethyl-9-decenoate, 9-DAEE from alkyl oleate and ethene. Side reactions may produce C5-C12 linear alpha olefins (alkenes) and C13-C24 esters. The metathesis reactions are equilibrium reactions and run accordingly. Shorter alkenes form from reactions of polyunsaturated C18:2 and C18:3 fatty acid esters with ethene. An example is given in Scheme 1 illustrating the chain shortening in metathesis reaction.

Scheme 1. Example of methathesis reaction of ethyl oleate and ethene producing 1-decene and ethyl-9-decenoate.

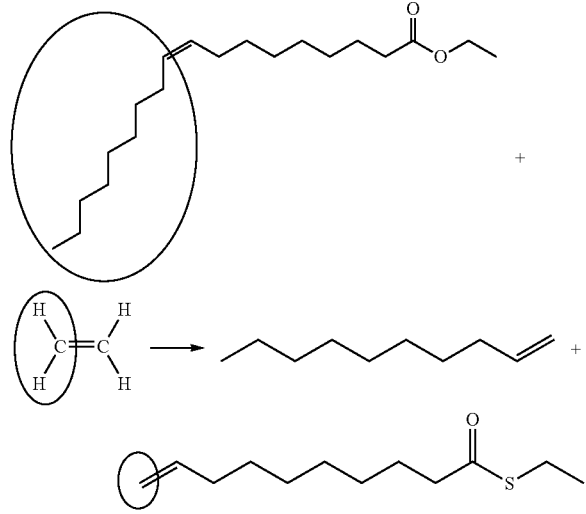

From the metathesis reaction, at least one renewable alkene and at least one fatty acid derived ester are recovered as products. Regarding the desired products, palm oil or palm oil fatty acids provide especially advantageous feed. PFAD is especially rich in oleic acid. Metathesis reaction between oleic acid ethyl ester and ethene produces 1-decene and ethyl-9-decenoate. Of these, 1-decene is especially attractive as a component for poly alpha olefin (PAO) production which again may be used for lubricant manufacture. Among other unsaturated C10-C15 fatty acid esters, ethyl-9-decenoate is an interesting precursor chemical for refining into oleo chemicals.

After the metathesis reaction, further step for product recovery in step e) may comprise metathesis product separation steps selected from evaporation, distillation or combinations thereof. Accordingly, the metathesis reaction product i.e. the reaction mixture from metathesis is led to evaporation, such as flash evaporation, wherein light alkenes, such as C2-C4 alkenes, are removed. The majority of this evaporate comprises the reagent used in excess in the metathesis reaction, which may optionally be recycled back to metathesis reaction from evaporation. Removal of said light alkenes enables recycling and provides better control for the following separation step, wherefrom other products are recovered.

Separation of the light alkene depleted metathesis products is conducted by product distillation. Some C5-C9 alkenes are recovered as alkene product, of which the major fraction, the C5-C7 alkenes, may be directed to renewable naphtha production.

As main product fractions, 1-decene and shortened esters, such as 9-DAEE are recovered from said product distillation. When recovered from present process, 1-decene is obtained in high purity, preferably over 99 w-%. It may further be reacted by polymerisation to renewable (bio-PAO) suitable for lubricant applications. 9-DAEE fraction recovered from the distillation is also of high purity, preferably over 98 w-%. It finds uses in manufacturing polymers, surfactants and/or solvents.

Metathesis Product Recovery

The process further comprises the recovery of at least one renewable alkene, comprising 1-decene and at least one fatty acid derived ester, comprising alkyl-9-decenoate, from products of the metathesis reaction.

As a specific embodiment, the metathesis product recovery can be described comprising i) an evaporation, wherefrom C2-C4 alkenes are recovered as evaporation overheads product, and recycled back to metathesis reaction, and a distillation of the evaporation bottom, wherefrom the renewable C5-C9 alkenes are recovered as distillation overheads product and the bottom product is directed to e)ii.

The fractional distillation in step e) may further comprise ii) a distillation of bottom product from evaporation i), wherefrom 1-decene is recovered as product distillation overheads product.

The fractional distillation in step e) may further comprise iii) a second distillation of bottom product from distillation ii), wherefrom a 9-decenoic acid alkyl ester, preferably 9-decenoic acid ethyl ester, is recovered as overheads product.

The fractional distillation in step e) may further comprise iv) hydrotreatment of the bottom product from second distillation iii), preferably hydrodeoxygenation and hydroisomerisation into at least one component selected from renewable diesel, renewable naphtha, renewable aviation fuel, and renewable gasoline.

Embodiments of the present process provide advantages over prior art processes through sophisticated use of these fractions.

Ketonisation

In relation to the present invention, ketonisation is applied according to specific embodiments and related to processing of a fatty acid ester fraction, preferably comprising at least 80%-wt of saturated fatty acid esters having a carbon chain length of C12-C16. In a specific embodiment, unexpected additional synergy has been found when the renewable alkene released during the ketonisation reaction is recycled and used as metathesis reagent.

The alcohol used for esterification, provides in the ketonisation reaction an alkene, that has been found to be usable in the metathesis reaction. Hence, when ethanol is reacted with fatty acids to produce esters in esterification, the ethene released during ketonisation of two of such esters can be recycled to metathesis reaction. The same applies to use of propanol, which yields propene from ketonisation. Preferably single alcohol and corresponding alkene for metathesis are used at a time.

As steps, this can be described as
  subjecting the fraction comprising fatty acid esters up to C16 or the fraction comprising saturated fatty acid esters having carbon chain length from C12 to C16, to ketonisation and hydrotreatment to produce renewable base oil comprising C31 hydrocarbons.
  wherein said ketonisation reaction conditions comprise a temperature from 200 to 300° C., a pressure from 1 to 3 MPa, a metal oxide ketonisation catalyst, preferably $TiO_2$, the presence of $CO_2$ gas flow, preferably a $CO_2$ flow from 0.25 to 1 gas/feed (w/w)), or a combination thereof.
  wherein said hydrotreatment comprises hydrodeoxygenation and isomerisation the obtained ketone stream into saturated hydrocarbon stream comprising C31 i-paraffins and n-paraffins.

Ketonisation reaction is an excellent deoxygenation reaction when deoxygenation, stability and energy density of products are the targets, as is often the case in production of base oils. Ketonisation removes 75 mol-% of the oxygen bound to carboxylic acid molecules without use of hydrogen. During the ketonisation reaction two fatty acid alkyl ester molecules are reacted together forming the corresponding linear ketone. One molecule of $CO_2$, water and two alkenes is simultaneously released during the reaction.

Ketonisation reaction may be carried out with high conversion, such as 95%, or 98%, or even 99.9%, and with excellent selectivity, such as 85%, or 92%, or even 95%, which is the reason why the renewable base oil yield can be almost theoretical. Due to the very selective ketonisation reaction only few or no light hydrocarbons are formed, therefore, bio-$CO_2$ recovered from the ketonisation reaction can be very pure, preferably at least 99% by volume, and it can be used for varying applications. Naturally, the ketones produced from the free fatty acid fractions obtained by the process of the present invention may also be used as chemicals for various applications other than base oil or fuel component production.

Ketonisation conditions are typically specified by the reactor temperature and pressure, the used catalyst, the carrier gas/feed ratio and weight hourly space velocity of the feed. The selected ranges may be combined according to need depending on the parameters to be optimized.

In the present process, a fatty acid ester fraction, comprising fatty acid esters having a carbon chain length of C12-C16 in an amount of at least 80%-wt of the total fraction weight, is subjected to ketonisation. Ketonisation product obtained from this reaction yields a product mixture that comprises C31 ketone. It is advantageous that the amount of said C31 ketone is at least 50%-wt, preferably at least 60%-wt, more preferably at least 70%-wt of the product mixture weight.

In the present invention, the ketonisation reaction may be carried out at a reaction temperature ranging from 300 to 400° C., more preferably from 330 to 370° C., most preferably from 340 to 360° C. The pressure range may be from 0.5 to 3.0 MPa, more preferably from 1.0 to 2.5 MPa, most preferably from 1.5 to 2.0 MPa, in the presence of a ketonisation catalyst. A suitable ketonisation catalyst comprises one or more metal oxide catalysts, preferably the metal of the metal oxide catalyst is selected from one or more of Na, Mg, K, Sc, Fe, Co, Ni, Cu, Zn, Sr, Y, Zr, Mo, Rh, Cd, Sn, La, Pb, Bi, Ti, Mn, Mg, Ca, Zr and rare earth metals. More preferably, the ketonisation catalyst is a metal oxide catalyst selected from the list consisting of one or more of: Ti, Mn, Mg, Ca, and Zr containing metal oxide catalyst. Most preferably, the catalyst is Ti containing metal oxide catalyst, such as $K_2O/TiO_2$ catalyst, or $TiO_2$ containing catalyst, such as $TiO_2$ catalyst. The weight hourly space velocity (WHSV) may be in the range from 0.25 to 3.0 h-1, preferably from 0.5 to 2.0 h-1, more preferably from 1.0 to 1.5 h-1. Ketonisation reaction may be performed in the presence of a gas in the range from 0.1 to 1.5 gas/feed ratio (w/w), preferably from 0.25 to 1.0, most preferably from 0.5 to 0.75, wherein the gas/feed ratio (w/w) means the mass of gas fed into the ketonisation reactor per the inlet fatty acid mass of the liquid feed into the ketonisation reactor. The gas is selected from one or more of: $CO_2$, $H_2$, $N_2$, $CH_4$, $H_2O$. Use of $H_2$ as gas provides advantages when applied in processes where the next phase also requires the presence of hydrogen, such as HDO. Then $H_2$ may flow through the reactor into said next phase. The most preferred gas is $CO_2$ as this is the product gas and may be efficiently recycled back to the feed, and it provides the most selective ketonisation reaction. According to a preferred embodiment, the ketonisation reaction conditions comprise the presence of $CO_2$ gas flow, preferably $CO_2$ flow from 0.25 to 1 gas/feed (w/w).

The alcohol used for esterification reaction, provides a corresponding alkene in the ketonisation reaction. This has been surprisingly found to provide an alkene reagent usable in the metathesis reaction. Hence, when ethanol is reacted with fatty acids to produce esters, the ethene released correspondingly from ketonisation of two esters can be recycled back to metathesis reaction. The same applies to use of propanol, which yields propene from ketonisation.

Hydrotreatment

Hydrotreatment refers to reactions in the presence of hydrogen such as hydrodeoxygenation (HDO), hydrogenation of double bonds, hydrocracking and/or hydroisomerisation, and it may also remove some metals. Within the context of the present process, hydrotreatment is needed for olefinic bond saturation and for removal of covalently bound oxygen from the fatty acid ester molecules and in some embodiments, from ketones. Typically, this means deoxygenation by hydrogenation i.e. hydrodeoxygenation (HDO) and hydrogenation of double bonds. Preferably, hydrotreatment comprises both hydrodeoxygenation and hydroisomerisation.

Hydrodeoxygenation

Hydrodeoxygenation of the fatty acid esters and optional fatty acids and optional ketones may be carried out as depicted e.g. in EP1741768A1, WO2007068795A1, WO2016062868A1 or EP2155838B1, and using a conventional hydrotreatment catalysts and hydrogen gas.

In one embodiment the hydrodeoxygenation takes place at reaction conditions comprising a temperature in the range from 100 to 500° C., preferably from 250 to 400° C., more preferably from 280-350° C., most preferably at temperature of 300-330° C.; and at a pressure in the range from 0.1 to 20 MPa, preferably from 0.2 to 8 MPa. Preferably, the weight hourly space velocity (WHSV) is in the range from 0.5 to 3.0 h$^{-1}$, more preferably from 1.0 to 2.5 h$^{-1}$, most preferably from 1.0 to 2.0 h$^{-1}$. Preferably, H2 flow is in the range from 350 to 900 nl H$_2$/l feed, more preferably from 350 to 750, most preferably from 350 to 500, wherein nl H$_2$/l means normal liters of hydrogen per liter of the feed into the HDO reactor, in the presence of a hydrodeoxygenation catalyst. The hydrodeoxygenation catalyst is preferably selected from Pd, Pt, Ni, Co, Mo, Ru, Rh, W, or any combination of these, such as CoMo, NiMo, NiW, CoNiMo on a support, wherein the support is preferably alumina and/or silica, preferably CoMo or NiMo on alumina support.

Isomerisation (Hydroisomerisation)

Isomerisation can be carried out in a conventional hydroisomerisation unit, such as those depicted in FI100248B, EP1741768A1, WO2007068795A1, WO2016062868A1 or EP2155838B1. Hydrogen is added into the isomerisation step.

Both the hydrodeoxygenation step and hydroisomerisation step may be conducted in the same reactor, and even in the same reactor bed. The hydroisomerisation catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerisation steps may be performed using NiW catalyst, or even in the same catalyst bed using the NiW catalyst for both the hydrodeoxygenation and isomerisation. The NiW catalyst may additionally result in more hydrocracking to diesel and naphtha products.

The hydroisomerisation step is preferably performed at a temperature from 250 to 400° C., more preferably from 280 to 370° C., most preferably from 300 to 350° C. Pressure is preferably from 1 to 6 MPa, more preferably from 2 to 5 MPa, most preferably from 2.5 to 4.5 MPa. The WHSV is preferably from 0.5 to 3 1/h, more preferably from 0.5 to 2 1/h, most preferably from 0.5 to 1 1/h, and H$_2$ flow from 100 to 800, more preferably from 200 to 650, most preferably from 350 to 500 n-liter H$_2$/liter feed, wherein n-liter H$_2$/l means normal liters of hydrogen per liter of the feed into the isomerisation reactor.

During hydroisomerisation n-paraffins are branched i.e. forming i-paraffins. Preferably, the conditions are chosen such that the branches are located at or near the terminal ends of the molecules, and therefore the cold flow properties of renewable base oil or optional renewable fuels are improved.

According to one embodiment, the fatty acid esters from metathesis product distillation bottom product may be subjected to both hydrotreatment comprising hydrodeoxygenation reaction conditions and to hydroisomerisation reaction conditions, simultaneously or in sequence, to yield a deoxygenated and isomerized paraffinic product stream comprising components suitable as renewable fuel components. According to a preferred embodiment, the saturated hydrocarbon stream comprises paraffins in the range of carbon number C15-C18 at least 70 wt-%, preferably at least 80 wt-%, more preferably at least 90 wt-% of the total weight of saturated hydrocarbon stream.

Products

Several renewable chemicals and components may be recovered from the present process. The products obtainable by the present process can be characterized as renewable chemicals, such as renewable alkenes, renewable fuel components, and renewable base oil. Such components may be used as such or in blends providing products fulfilling specifications set for said products.

The reference "renewable" in relation to the products obtainable from the present process, refers to high renewable carbon content in the products. Typically, renewable carbon predominates that of fossil origin. In specific cases, all carbon of a product may be of renewable origin. However, it is generally accepted that some reagents, such as hydrogen, used in the processes may originate from non-renewable sources and yet the product is considered renewable. The renewable content may be determined from both the starting materials and the products, i.e. by isotopic distribution involving $^{14}$C, $^{13}$C and/or $^{12}$C as described in ASTM D6866. According to the present disclosure the renewable products obtained, such as diacids, have a $^{14}$C concentration of the total carbon content that is clearly measurable and distinct from that of fossil products, preferably more than 50 wt-%, more preferably more than 90 wt-%, most preferably more than 98 wt-%, such as 99 wt-% or higher.

Metathesis products recoverable from fractionation comprise various alkenes. Such C10-C12 alkenes may be used for lubricant or special chemicals' manufacture. Depending on the reagent used in the metathesis reaction, a double bond is typically at alpha, beta or gamma position. Metathesis products recoverable from separation may comprise 1-decene, 3-dodecene, 1,4-decadiene, 3,5-dodecadiene, of which preferred are 1-decene and 3-dodecene.

In the metathesis feed, an abundant reacting fatty acid ester is C18:1, thus alkyl oleate. When using ethene as metathesis reagent, the most interesting C10 alkene fraction comprises 1-decene, and some 1,4-decadiene and 1,4,7-decatriene. When using propene or 2-butene as metathesis reagent, the recovered C11 alkene fraction comprises 2-undecene, and some 2,5-undecadiene and 2,5,8-undecatriene. With propene, the C10 fraction is equally present. Respectively, when using 1-butene as metathesis reagent, the main product is recovered as C12 fraction comprising 3-dodecene. Further, with 1-butene, the C10 fraction is again equally present.

Polyunsaturated fatty acid alkyl esters produce shorter alkenes as well.

With regard to fatty acids as metathesis products, the products formed from alkyl oleate are especially interesting. With ethene as metathesis reagent, the C10 ester fraction is of interest, especially 9-decenoate. When using propene or 2-butene as metathesis reagent, the prevailing fraction is C11 and therein 9-undecenoate. Respectively, when using 1-butene as metathesis reagent the C12 ester fraction and 9-dodecenoate are the main products. All said reagents, except 2-butene produce C10 esters. The fatty acid esters recoverable from metathesis comprise unsaturated fatty acid esters having thus varying carbon chain lengths. Many C10-C12 fatty acid esters may be used for oleochemicals' manufacture such as for fatty alcohols, soaps, dimer acids, esters, amides, amines, sulfonates, etc.

Polyunsaturated fatty acid alkyl esters produce longer metathesis product fatty acid esters, such as linoleic acid (C18:2) with ethene a C13-ester fraction, with propene a C14-ester fraction etc.

Products with terminal a C═C double bond are most desired. Further, monounsaturated fatty acid esters are preferred over polyunsaturated products.

The renewable content for any renewable product herein may be determined from both the starting materials and the products by isotopic distribution involving $^{14}$C, $^{13}$C and/or $^{12}$C as described in ASTM D6866 (2018).

Ketonisation and hydrotreatment may be applied in combination to the fraction recovered from step c comprising saturated fatty acid esters having carbon chain length from C12 to C16 in a cumulative amount of at least 80%-wt, preferably at least 90%-wt of the total fraction weight. Further, hydrotreatment in step p2) may comprise both hydrodeoxygenation and isomerisation the obtained ketone stream into saturated hydrocarbon stream. When applied to palmitates, ketonisation and hydrotreatment provide hydrocarbon stream comprising C31 i-paraffins and n-paraffins. The product therefrom is a renewable base oil meeting the API group III specifications, more specifically a renewable base oil fulfilling the API Group III base oil specifications containing ≤0.03 wt-% sulfur, having a viscosity index of ≥120, having carbon numbers of at least C18, containing at least 90%-wt of saturated hydrocarbons, the saturated hydrocarbons consisting of paraffinic and naphthenic compounds and contains based on FIMS analysis mononaphthenes from 1 to 6%-wt. As to structure, preferably said base oil comprises or consists essentially of C31 paraffins.

The fraction comprising saturated C18 fatty acid esters, may be reacted to oleochemicals, which find uses as diesel component (FAME or renewable diesel) or as raw material for soaps, lubricating agents and candles.

According to a preferred embodiment, the present process through its different branches provides combined renewable products, hence renewable alkenes, renewable oleochemicals and renewable base oil, and optionally renewable paraffinic fuels. The term "renewable paraffinic fuel" defines said products being saturated hydrocarbons suitable for use as components for certain fuel grades. Paraffinic refers to their character as alkanes, straight chain or branched, not containing heteroatoms or double bonds.

EXPERIMENTAL

Example 1, Conversion of PFAD into Renewable Products

The process outset corresponds to the embodiment described in FIG. 1. The steps leading to and relating to fractional distillation and metathesis reaction are disclosed in detail. Further processing of streams separated from said main stream are described generally, as the details may be found in prior art.

Here, palm oil fatty acid distillate (PFAD) was selected as representative feedstock. PFAD (palm oil fatty acid distillate) used was a by-product of physical refining of crude palm oil products. It was composed of free fatty acids (81.7%), glycerides (14.4%), squalene (0.8%), vitamin E (0.5%), sterols (0.4%) and other substances (2.2%). Relevant characteristics for this feedstock are the significant amounts of methyl oleate and methyl palmitate.

Intermediates and products were identified and characterized by gas chromatography after each reaction step.

Esterification

The feedstock was first subjected to esterification of fatty acids in the presence of methanol. Reaction was conducted at conditions common for esterification. A fatty acid ester containing stream was obtained, having methyl ester distribution depicted in Table 2.

TABLE 2

Carbon chain length distribution after esterification.

| Ester | wt-% |
|---|---|
| 14:0ME | 1.2 |
| 16:0ME | 46.3 |

TABLE 2-continued

Carbon chain length distribution after esterification.

| Ester | wt-% |
|---|---|
| 18:0ME | 4.3 |
| 18:1ME | 35.7 |
| 18:2ME | 9.1 |
| 18:3ME | 0.3 |
| Others | 3.1 |

The feedstock enters the process and is first subjected to fractional distillation. Water and methanol are removed in the lightest fraction. Fatty acid C16 and C18 esters are separated to corresponding fractions from the mixture as given in Table 3.

TABLE 3

Separation of C16 esters and C18 esters from the ester mixture by distillation with a packed column.

| Fraction | Pressure (mbar) | Bottom temperature (° C.) | Head temperature (° C.) | Composition |
|---|---|---|---|---|
| I | 10 | 195 | 171 | 94.1 wt-% C16:0 ME 5.9 wt-% others |
| II | 8 | 205 | 192 | 8.4 wt-% C18:0 ME 70.3 wt-% C18:1 ME 17.9 wt-% C18:2 ME 0.6 wt-% C18:3 ME 2.8 wt-% others |

Fraction I, hence the fraction comprising saturated fatty acid esters having carbon chain length of C16 in an amount of at least 90%-wt of the total fraction weight is conducted to processing into renewable base oil through further process steps not shown in detail here.

Fraction II, hence the fraction comprising at least 80%-wt of the total fraction weight of unsaturated C18 fatty acid esters, is fed to metathesis reaction.

A bottom product from distillation may be discarded. It typically contains remaining glycerides and some heavier fatty acid methyl esters.

The inventors have surprisingly found that fractional distillation provides several advantages. Since some metathesis catalysts are considered sensitive to impurities, such as alcohols and peroxides, careful purification has been part of prior art metathesis reactions. Especially, if the esterified intermediate is stored, peroxides form spontaneously. The distillation conditions decompose peroxides and remove volatile polar components like peroxide decomposition products from the fraction directed to metathesis. Further, since roughly half of the feed is removed in case of palm based esters and directed to other processing, the feed entering metathesis is correspondingly reduced. This is beneficial because productivity of metathesis can be increased by increasing the concentration of olefinic bonds in the reaction mixture.

Metathesis

Fraction II from Table 3 and a metathesis catalyst solution were loaded under nitrogen atmosphere to a stainless-steel reactor equipped with a magnetic stirrer, pressure and temperature measurement, a sampling tube and a gas inlet. The catalyst used was a commercially available metathesis catalyst, which was used in an amount instructed by the provider. The reactor was closed and pressurized with 6 barg of ethene. Optionally the pressure may be provided with a gas inert to the metathesis and ethene fed only in amounts needed for the reactions. Vigorous mixing was started and temperature was increased to 50° C. The pressure was kept constant for 6 h by feeding more ethene to replace that reacted. After 18 hours the reactor contents were analyzed with GC. The main components are methyl 9-decenoate (36 wt-%), decenes (23 wt-%) and unreacted C18 esters (20 wt-%).

The reaction mixture from metathesis is led to evaporation at ambient temperature and pressure, which removes gaseous components, the inert gas and ethene, the reagent used in excess in the metathesis reaction. This fraction may optionally be recycled back to metathesis reaction.

After removal of the gaseous components, the main components can be separated by distillation in a packed column. Heating to 120° C. under normal pressure removes C5-C7 alkenes that are formed in metathesis. This fraction can be utilized in renewable naphta production. Decenes and methyl 9-decenoate can then be separated as in Table 4.

TABLE 4

Separation of C10 alkenes and C10 methyl ester by distillation.

| Pressure (mbar) | Bottom temperature (° C.) | Head temperature (° C.) | Distillate composition |
|---|---|---|---|
| 30 | 150 | 70 | 99.7 wt-% C10 alkenes |
| 28 | 170 | 122 | 99.8 wt-% methyl 9-decenoate |

A further heavy fraction can be recovered as a distillate that contains unreacted C18 methyl esters and C13-C18 alkenes and methyl esters that are formed in metathesis as side products. This fraction can be directed to the process producing renewable diesel. The remaining bottom product (less than 5%-wt of the total feed weight) contains heavy diesters and after catalyst removal is typically combusted.

Some metathesis catalysts are prone to isomerize C═C bonds in distillation conditions. If such a catalyst is used, the distillation step can be preceded by some deactivation or removal steps for these catalysts that are described in the literature.

The invention claimed is:

1. A process for combined renewable alkene and renewable chemical production from a glyceride containing feedstock, the process comprising:
   a) providing the glyceride containing feedstock containing free fatty acids, fatty acid glycerides selected from monoglycerides, diglycerides and triglycerides of fatty acids, and/or a mixture thereof, wherein the feedstock contains a compound having at least one carbon-carbon double bond;
   b) subjecting the feedstock to esterification reaction in a presence of a C1-C4 monoalcohol, to yield a product having a fatty acid ester stream;
   c) subjecting the product from step b) to fractional distillation to provide at least three fractions of: a gas fraction containing water and C1-C4 alcohols; a fraction containing fatty acid esters up to C16 for producing renewable base oil meeting API group III specifications; and a fraction containing alkyl esters of unsaturated C18 fatty acids;
   d) subjecting the fraction containing alkyl esters of unsaturated C18 fatty acids to metathesis reaction conditions in a presence of a C2-C4 alkene to obtain metathesis products containing renewable alkenes, and fatty acid derived esters; and
   e) recovery of at least one renewable alkene containing 1-decene, and at least one fatty acid derived ester containing alkyl-9-decenoate, from the products of step d).

2. The process according to claim 1, wherein the fractional distillation in step c) provides:
   at least one fraction containing water and C1-C4 monoalcohol, in a cumulative amount of at least 80%-wt of a total fraction weight;
   at least one fraction containing saturated fatty acid esters having carbon chain length from C12 to C16 in a cumulative amount of at least 80%-wt and/or at least 90% wt of the total fraction weight;
   at least one fraction containing alkyl esters of unsaturated C18 fatty acids; and
   an optional bottom product from the fractional distillation containing >C18 fatty acid esters and glycerol.

3. The process according to claim 2, wherein the fraction containing alkyl esters of unsaturated C18 fatty acids comprises:
   fatty acid esters having a carbon chain length of C18, in a cumulative amount of at least 80%-wt of a total fraction weight.

4. The process according to claim 3, wherein step e) comprises:
   metathesis product separation steps selected from evaporation, distillation or combinations thereof.

5. The process according to claim 4, wherein step e) comprises:
   i) an evaporation, wherefrom the C2-C4 alkenes are recovered as an evaporation overheads product, and recycled back to a metathesis reaction, and a distillation of an evaporation bottom, wherefrom renewable C5-C9 alkenes are recovered as a distillation overheads product and the bottom product is obtained.

6. The process according to claim 5, wherein step e) comprises:
   ii) a distillation of the bottom product from distillation i), wherefrom 1-decene is recovered as a product distillation overheads product.

7. The process according to claim 6, wherein step e) comprises:
   iii) a second distillation of the bottom product from distillation ii), wherefrom alkyl-9-decenoate and/or ethyl-9-decenoate, is recovered as an overheads product.

8. The process according to claim 7, wherein step e) comprises:
   iv) hydrotreatment of the bottom product from second distillation iii), by hydrodeoxygenation and hydroisomerisation into at least one component selected from renewable diesel, renewable naphtha, renewable aviation fuel, and renewable gasoline.

9. The process according to claim 1, wherein the metathesis reaction conditions in step d) comprise:
   a temperature from 20 to 120° C., a pressure from 0.1 to 3 MPa and a metathesis catalyst.

10. The process according to claim 1, wherein the C1-C4 monoalcohol used in step b) is selected from at least one or more of methanol, ethanol, 1-propanol, 2-propanol, 1-butanol and 2-butanol, and/or a mixture thereof and/or from bio based monoalcohols, and/or from bio based ethanol.

11. The process according to claim 1, wherein the C2-C4 alkene is ethene.

12. The process according to claim 2, comprising:
   subjecting the fraction containing fatty acid esters up to C16, or the fraction containing saturated fatty acid esters having carbon chain length from C12 to C16, to ketonisation and hydrotreatment to produce renewable base oil meeting the API group III specifications.

13. The process according to claim 12, wherein the monoalcohol used in step b) is ethanol, the ketonisation releases ethene, and the ethene thereby produced is recycled back to metathesis reaction in step d).

14. The process according to claim 1, wherein the metathesis products comprise:
ethyl-9-decenoate.

15. The process according to claim 1, comprising:
hydrotreatment of the bottom product containing >C18 fatty acid esters from separation in step c).

16. Process for providing a metathesis reaction, the process comprising:
conducting the fractional distillation of claim 1 as pretreatment for the metathesis reaction of fatty acid esters according to the process of claim 1.

17. Process according to claim 16, in a combined renewable base oil and renewable alkene production.

18. Process according to claim 17, comprising:
producing a renewable fuel.

19. The process according to claim 1, wherein the fractional distillation in step c) provides:
the bottom product from the fractional distillation containing >C18 fatty acid esters and glycerol.

20. The process according to claim 2, wherein the fraction containing saturated fatty acid esters having carbon chain length from C12 to C16 comprises:
saturated fatty acid esters having a carbon chain length from C12 to C16 in a cumulative amount of at least 90%-wt of the total fraction weight.

21. The process according to claim 2, wherein the fraction containing alkyl esters of unsaturated C18 fatty acids comprises:
fatty acid esters having a carbon chain length of C18 in a cumulative amount of at least 90%-wt of a total fraction weight.

* * * * *